United States Patent
Sirdesai et al.

(10) Patent No.: US 12,370,133 B2
(45) Date of Patent: Jul. 29, 2025

(54) METHODS FOR MANUFACTURING ARGININE DENTIFRICE

(71) Applicant: Colgate-Palmolive Company, New York, NY (US)

(72) Inventors: Amit U. Sirdesai, Mumbai (IN); Devendra Chavan, Mumbai (IN); Shashank Potnis, Piscataway, NJ (US); Maya Bhansali, Mumbai (IN); Divya Iyer, Mumbai (IN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/210,180

(22) Filed: Mar. 23, 2021

(65) Prior Publication Data

US 2021/0308027 A1  Oct. 7, 2021

(30) Foreign Application Priority Data

Mar. 24, 2020 (IN) .............................. 202011012813

(51) Int. Cl.
| | |
|---|---|
| *A61K 8/44* | (2006.01) |
| *A61K 8/24* | (2006.01) |
| *A61K 8/25* | (2006.01) |
| *A61K 8/60* | (2006.01) |
| *A61Q 11/00* | (2006.01) |

(52) U.S. Cl.
CPC .................. *A61K 8/44* (2013.01); *A61K 8/24* (2013.01); *A61K 8/25* (2013.01); *A61K 8/60* (2013.01); *A61Q 11/00* (2013.01)

(58) Field of Classification Search
CPC . A61K 8/60; A61K 8/25; A61K 8/345; A61K 8/44; A61K 8/24; A61K 2800/80; A61Q 11/00
See application file for complete search history.

(56) References Cited

U.S. PATENT DOCUMENTS

| | | |
|---|---|---|
| 5,370,865 A | 12/1994 | Yamagishi et al. |
| 10,543,163 B2 | 1/2020 | Santarpia, III et al. |
| 2009/0202450 A1 | 8/2009 | Prencipe et al. |
| 2013/0224270 A1* | 8/2013 | Robinson ............... A61Q 11/00 424/401 |
| 2014/0305461 A1 | 10/2014 | Pimenta et al. |
| 2017/0020801 A1 | 1/2017 | Santarpia et al. |
| 2018/0015016 A1 | 1/2018 | Huang et al. |
| 2018/0207073 A1 | 7/2018 | Poth et al. |
| 2018/0221259 A1 | 8/2018 | Potanin et al. |

FOREIGN PATENT DOCUMENTS

| | | | |
|---|---|---|---|
| CN | 105792800 | | 7/2016 |
| CN | 107530238 | | 1/2018 |
| CN | 109381350 | * | 2/2019 |
| WO | 2009/099453 | | 8/2009 |
| WO | 2012/057739 | | 5/2012 |
| WO | 2013/089734 | | 6/2013 |
| WO | WO 2016/176180 | * | 11/2016 |

OTHER PUBLICATIONS

International Search Report and the Written Opinion of the International Searching Authority issued in International Application PCT/US2021/023725 mailed Jul. 12, 2021.
Chen Guanrong et al., 1993, Encyclopedia of Chemical Engineering, Chemical Industry Press, vol. 3, pp. 773-775, Translated paragraphs only.
Li, Liangzhu et al., The latest biochemical drug preparation technology, China Medical Science Press, 1st edition, published Mar. 31, 2001, pp. 68-69, with English Summary, English Content Considered only.

* cited by examiner

*Primary Examiner* — Lezah Roberts

(57) ABSTRACT

Disclosed herein are improved methods for the manufacture of arginine-based dentifrice compositions comprising the use of a solution of arginine free base (e.g., L-arginine) in concentrated aqueous sorbitol solution.

19 Claims, No Drawings

METHODS FOR MANUFACTURING ARGININE DENTIFRICE

CROSS-REFERENCE TO RELATED APPLICATIONS

The instant application is a U.S. Non-Provisional application which claims priority to Indian Application No. 202011012813, filed on Mar. 24, 2020, the contents of which are hereby incorporated by reference in its entirety.

BACKGROUND

Arginine and other basic amino acids have been proposed for use in oral care and are believed to have significant benefits in combating cavity formation and tooth sensitivity. Combining these basic amino acids with minerals having oral care benefits, e.g., fluoride and calcium, to form an oral care product having acceptable long-term stability, however, has proven challenging. In particular, the basic amino acid may raise the pH and facilitate dissociation of calcium ions that can react with fluoride ions to form an insoluble precipitate. Moreover, the higher pH has the potential to cause irritation. At neutral pH or acidic pH, however, a system utilizing arginine bicarbonate (which the art teaches is preferred) may release carbon dioxide, leading to bloating and bursting of the containers. Moreover, it might be expected that lowering the pH to neutral or acidic conditions would reduce the efficacy of the formulation because the arginine may form an insoluble arginine-calcium complex that has a poorer affinity for the tooth surface, and moreover, that lowering the pH would reduce any effect the formulation might have on buffering cariogenic lactic acid in the mouth.

Arginine-based dentifrices, such as toothpastes, are known, including such toothpastes as ProClude® and DenClude® toothpaste. These toothpastes contain arginine bicarbonate and precipitated calcium carbonate, but not fluoride. The carbonate ion is believed to have cariostatic properties, and the calcium is believed to form a complex with arginine to provide a protective effect.

More recently, the use of natural calcium carbonate (e.g., chalk or limestone) as an abrasive in dentifrice compositions has become popular because this material typically has a well-defined crystal structure (making it very hard). It is generally quarried, and must be milled to size. Natural calcium carbonate abrasive provides good tooth cleaning and stain removal, but because it is highly abrasive, it has been considered undesirable for persons having sensitive teeth. Precipitated calcium carbonate is more friable and less abrasive, resulting in less damaging abrasion to enamel, which is good for sensitive teeth, but also it typically provides less effective cleaning.

Another effective calcium abrasive that has seen increasing use is dicalcium phosphate (DiCal).

Accordingly, dentifrice formulations have been developed which comprise arginine in free base form, combined with beneficial minerals such as fluoride and calcium, and an optimized abrasive system to provide effective cleaning without damaging abrasivity, particularly for people having sensitive teeth.

While compositions based on the foregoing observations are known, it has proven difficult to manufacture these compositions on a large scale due to the difficulty of working with arginine free base (e.g., L-arginine) on a large plant scale. For example, typically toothpaste manufacturing plants operate on a batch process using batch sizes up to 5-6 tons. At the typical concentrations at which arginine freebase is utilized in such toothpastes, this has required the manual manipulation of quantities of arginine up to 78 kilograms. Such manual manipulation is very difficult, even when using smaller bags of 20-30 kg arginine each. The increase in the production rate of arginine-based dentifrices has made improved methods necessary in order to provide optimal safety and efficiency.

Previous efforts to overcome this problem have involved the attempted automation of these manual processes. For example, the distribution of solid arginine powder in a manufacturing plant using either pressure or vacuum as the moving force has been attempted, but suffers unacceptable losses due to aerosolization or surface trapping. Arginine powder is both hygroscopic and sticky, making automated delivery of powdered material very difficult.

The problem is particularly exacerbated by the fact that arginine is an active ingredient in dentifrice compositions, and therefore, it's concentration must be tightly controlled according to manufacturer or regulatory specifications.

There is thus a need for improved methods of handling arginine for the manufacture of arginine-based dentifrice products.

BRIEF SUMMARY

It has now been discovered that arginine free base (e.g., L-arginine) can be effectively solubilized in concentrated aqueous sorbitol solution. While sorbitol is a commonly used humectant in the dentifrice industry, and it is not uncommon to formulate dentifrice compositions having a final concentration of up to 80% by weight sorbitol, it has not previously been disclosed to use sorbitol solution as the vehicle for introducing arginine free base into a formulation as a manufacturing process step.

The discovery that concentration aqueous sorbitol solution can effectively solubilize arginine free base (e.g., L-arginine) for manufacturing handling is particularly unexpected because water is not similarly effective for this purpose. Arginine free base can be fully solubilized in water at a temperature of 80 to 85° C. However, it has been found that the arginine in such a solution is unstable and undergoes degradation, especially at such a high temperature, and this leads to waste of arginine material and impurities in the final dentifrice product. Operating with water at a lower temperature, however, results in aqueous slurries that are difficult to work with in a manufacturing plant. Water is also prone to microbial growth that can contaminate the final dentifrice product.

In addition, many current arginine-based dentifrice compositions are low-water compositions, having final water content of less than 20% w/w, even as low as 5 to 10% w/w. At lower solubilization temperatures the volume of water necessary to use arginine solution for manufacturing would result in formulations with excessive water content.

The present invention therefore provides a method of manufacturing an arginine-based dentifrice comprising the steps of (1) forming a solution of arginine free base (e.g., L-arginine) in concentrated aqueous sorbitol, and (2) combining the arginine/sorbitol solution with one or more other orally acceptable ingredients.

The invention further provides dentifrice compositions made according to the present synthetic methods.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The invention therefore provides a method (Method 1) of manufacturing an arginine-based dentifrice comprising the steps of (1) forming a solution of arginine free base (e.g., L-arginine) in concentrated aqueous sorbitol, and (2) combining the arginine/sorbitol solution with one or more other orally acceptable ingredients. In further embodiments of Method 1, the present disclosure provides:
- 1.1. Method 1, wherein the concentrated aqueous sorbitol is a 60-80 wt % aqueous sorbitol solution (e.g., about 70 wt % sorbitol);
- 1.2. Method 1 or 1.1, wherein the concentrated aqueous sorbitol is derived from the hydrogenation of glucose;
- 1.3. Method 1.1 or 1.2, wherein the concentrated aqueous sorbitol consists essentially of sorbitol and water (e.g., having less than 5 wt % or less than 2 wt % of any other components, such as glucose);
- 1.4. Method 1 or any of 1.1 et seq., wherein the arginine is L-arginine;
- 1.5. Method 1 or any of 1.1 et seq., wherein the solution of arginine in concentrated aqueous sorbitol of step (1) consists essentially of arginine, sorbitol and water, and optionally a base (e.g., sodium bicarbonate);
- 1.6. Method 1 or any of 1.1 et seq., wherein the solution of arginine in concentrated aqueous sorbitol of step (1) comprises from 1 to 30% w/w of arginine, e.g., 1 to 20% w/w arginine, or 1 to 10% w/w arginine, or about 5% w/w arginine;
- 1.7. Method 1 or any of 1.1 et seq., wherein the solution of arginine in concentrated aqueous sorbitol of step (1) is formed at room temperature (e.g., 15 to 30° C., or 20 to 25° C.);
- 1.8. Method 1 or any of 1.1 et seq., wherein the solution of arginine in concentrated aqueous sorbitol of step (1) is formed at elevated temperature (e.g., 30 to 70° C., or 60 to 70° C.);
- 1.9. Method 1 or any of 1.1 et seq., wherein the solution of arginine in concentrated aqueous sorbitol of step (1) is chemically and physically stable for at least 5 days, or at least 2 weeks, or at least 1 month, or at least 3 months (e.g., no signs of chemical degradation of arginine or physical alteration or degradation of the solution, such as, precipitation, crystallization, or color change);
- 1.10. Method 1 or any of 1.1 et seq., wherein the solution of arginine in concentrated aqueous sorbitol of step (1) is microbially stable for at least 5 days, or at least 2 weeks, or at least 1 month, or at least 3 months (e.g., no signs of microbial contamination or microbial growth in excess of safety margins);
- 1.11. Method 1 or any of 1.1 et seq., wherein the solution of arginine in concentrated aqueous sorbitol of step (1) has a pH of 7.5 to 11, e.g., 8 to 11, or 9 to 11, or 10 to 11, or about 10.6;
- 1.12. Method 1 or any of 1.1 et seq., wherein the solution of arginine in concentrated aqueous sorbitol of step (1) is used less than 24 hours after formation in step (2), e.g., less than 12 hours after formation, or less than 6 hours after formation, or less than 3 hours after formation, or less than 1 hour after formation, or within 30 minutes of formation, or within 5 minutes of formation;
- 1.13. Method 1.12, wherein the solution of arginine in concentrated aqueous sorbitol of step (1) is used in step (2) immediately after formation;
- 1.14. Method 1 or any of 1.1 et seq., wherein step (2) comprises the step of adding the solution of arginine in concentrated aqueous sorbitol of step (1) to a mixture of one or more orally acceptable ingredients (e.g., a solution, suspension or slurry of one or more orally acceptable ingredients, optionally in an orally acceptable solvent or mixture of solvents);
- 1.15. Method 1 or any of 1.1 et seq., wherein step (2) comprises the step of adding one or more orally acceptable ingredients to the solution of arginine in concentrated aqueous sorbitol of step (1) (e.g., to form a new solution, suspension or slurry of the combined orally acceptable ingredients);
- 1.16. Method 1 or any of 1.1 et seq., wherein the method further comprises the step(s) of combining one or more orally acceptable ingredients together, optionally including one or more orally acceptable solvents, either prior to or concurrently with step (1) or step (2), or subsequent to the formation of the mixture of step (2), and thereafter combining this mixture with the mixture from step (2);
- 1.17. Method 1 or any of 1.1 et seq., wherein any one or more of the one or more orally acceptable ingredients are selected from water, abrasives, humectants (e.g., other than the concentrated aqueous sorbitol), surfactants, thickeners, fluoride sources, anticaries agents, desensitizing agents, antibacterial agents, whitening agents, pH adjusting agents (e.g., acids or bases), preservatives, colorants, flavorants, and sweeteners.
- 1.18. Method 1.17, wherein the abrasives are selected from silica (e.g., abrasive silica), sodium silicate, natural calcium carbonate (NCC), precipitated calcium carbonate (PCC), dicalcium phosphate (DiCal);
- 1.19. Method 1.17, wherein the humectants are selected from sorbitol (e.g., concentrated aqueous sorbitol), glycerin, and propylene glycol, provided that if such humectants include sorbitol this is in addition to the sorbitol provided by the solution of arginine in concentrated aqueous sorbitol of step (1);
- 1.20. Method 1.17, wherein the surfactant is an anionic surfactant, e.g., sodium lauryl sulfate;
- 1.21. Method 1.17, wherein the thickener is selected from thickening silica, carboxymethyl cellulose (e.g., sodium carboxymethyl cellulose), carrageenan, and xanthan gum;
- 1.22. Method 1.17, wherein the fluoride source is selected from sodium fluoride, stannous fluoride, and sodium monofluorophosphate;
- 1.23. Method 1.17, wherein the anticaries agent is selected from tetrasodium pyrophosphate, tetrapotassium pyrophosphate, sodium tripolyphosphate, potassium tripolyphosphate, and mixtures thereof;
- 1.24. Method 1.17, wherein the pH adjusting agents are selected from sodium bicarbonate, sodium hydroxide, hydrochloric acid, phosphoric acid, and citric acid;
- 1.25. Method 1.17, wherein the preservatives are selected from benzoic acid and benzyl alcohol;
- 1.26. Method 1.17, wherein the desensitizing agent is selected from potassium chloride and potassium nitrate;
- 1.27. Method 1.17, wherein the antibacterial agents are selected from zinc chloride, zinc phosphate, zinc citrate, zinc oxide, zinc pyrophosphate, zinc lactate, stannous chloride, stannous fluoride, stannous phosphate, stannous pyrophosphate, or any combination thereof;

1.28. Method 1 or any of 1.1 et seq., wherein the product of method has a water content of less than 20 wt % by weight of the composition, e.g., 1 to 15% by weight, or 1 to 10% by weight, or 1 to 5% by weight, or 5 to 10% by weight;

1.29. Method 1 or any of 1.1 et seq., wherein the product of the method comprises arginine in an amount of 0.5 to 5% by weight of the composition, e.g., 1.0 to 3.0% by weight or 1.0 to 2.0% by weight, or about 1.5% by weight;

1.30. Method 1 or any of 1.1 et seq., wherein the product of the method comprises sorbitol in an amount of 5 to 90% by weight of the composition, e.g., 10 to 50% by weight, or 15 to 30% by weight, or 20 to 25% by weight, or about 21% by weight of the composition;

1.31. Method 1 or any of 1.1 et seq., wherein the product of the method comprises abrasives in a total amount of 10 to 70% by weight of the composition, e.g., 20 to 60% by weight, or 30 to 50% by weight of the composition;

1.32. Method 1 or any of 1.1 et seq., wherein the product of the method comprise any one or more ingredients described herein each in an amount of 0.1 to 30% by weight of the composition, e.g., 0.1 to 20% by weight, or 0.1 to 15% by weight, or 0.1 to 10% by weight or 0.1 to 5% by weight, or 0.1 to 1% by weight, 1 to 10% by weight, or 10 to 20% by weight, or 20 to 30% by weight, or 10 to 15% by weight, or 15 to 20% by weight of the composition;

1.33. Method 1 or any of 1.1 et seq., wherein the method comprises the step of transferring through pipes the solution of arginine free base in concentrated aqueous sorbitol derived from step (1), for example, from a tank or reactor in which step (1) occurred and/or into a tank or reactor in which step (2), or a later step, will occur;

1.34. Method 1 or any of 1.1 et seq., wherein the method comprises the steps of combining the arginine free base (e.g., L-arginine), the concentrated aqueous sorbitol (e.g., 70% w/w), and optionally the base (e.g., sodium bicarbonate), in a first tank or reactor, which is followed by a period of mixing, optionally until a homogenous solution is formed, followed by adding one or more additional ingredients into the first tank or reactor, such as water and/or potassium nitrate; and simultaneously in a second tank or reactor combining one or more other ingredients (e.g., a fluoride source, such as sodium monofluorophosphate, and/or one or more sweeteners (e.g. sodium saccharin), flavors, colors, or other minor ingredients) in an orally acceptable solvent (e.g., water and/or one or more humectants) to form a premix (e.g. gel); and adding any additional ingredients, separately or together, to the premix; and thereafter adding the premix from the second tank or reactor into the first tank or reactor, or vice versa; and thereafter adding any further ingredients to the tank or reactor having the combined components from the first tank or reactor and the second tank or reactor, e.g., one or more of carrageenan, sodium silicate; and thereafter transferring the resulting mixture to a third tank or reactor (e.g., a mixing tank or reactor), and thereafter adding to this tank or reactor one or more of abrasives (e.g., PCC and/or NCC), thickeners (e.g., thickening silica), surfactants (e.g., SLS), preservatives (e.g., benzyl alcohol), colors, and flavors, optionally followed by or concurrent with de-aerating the mixture, and optionally with adding any ingredients (e.g., surfactant) under vacuum;

1.35. Method 1 or any of 1.1 et seq., wherein the product of the method has a composition according to Table 2 hereinbelow;

1.36. Method 1 or any of 1.1 et seq., wherein the product of the method has a composition according to Table 1 hereinbelow;

1.37. A dentifrice composition made according to Method 1 or any of Methods 1.1 to 1.36; 1.38. Dentifrice 1.37, wherein the dentifrice is a toothpaste;

1.39. Dentifrice 1.37 or 1.38, wherein the dentifrice has a composition according to Table 1 or Table 2 hereinbelow.

Unless stated otherwise, all percentages of composition components given in this specification are by weight based on a total composition or formulation weight of 100%.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1: Methods

L-arginine is dissolved in 70% w/w aqueous sorbitol solution at room temperature at a weight ratio of 1.5:30. The resultant solution is homogenous and contains about 4.8% by weight of L-arginine, about 29% by weight of water, and about 67% by weight of sorbitol. The solution has a pH of 10.6.

The solution is tested in a standard microbial assay and it passes the test both at the initial testing (immediately after formation of the solution), as well as 24 hours after formation and 1 week after formation. Briefly, a microbial contamination check test is performed whereby a test material solution is aseptically sampled in an enriched medium and incubated for 4-5 days. Any microorganisms present will form colonies visible to naked eye, and these are counted and the results compared at different levels of dilution.

The solution is assayed by HPLC at 2 days after formation and 7 days after formation, and it is measured to have 4.61% by weight of arginine and 4.69% by weight of arginine, respectively, at these two time points. These measured values correspond to 98% and 99% of the theoretical amount and are both within the error range of the assay as not different from 100%.

Example 2: Dentifrice Compositions

The solution of Example 1 is used to prepare a dentifrice composition having the formula shown in Table 1 below:

TABLE 1

| Ingredient | Weight % |
| --- | --- |
| Sorbitol (70% Aq.) | 30 |
| Carrageenan | 0.8 |
| Sodium Saccharin | 0.27 |
| Sodium monofluorophosphate | 0.76 |
| Sodium bicarbonate | 0.5 |
| Water | q.s. (e.g., 14%) |
| Sodium silicate | 1.0 |
| Thickening silica | 1.0 |
| PCC | 22 |
| NCC | 23 |
| Titanium dioxide | 1.0 |
| Sodium lauryl sulfate | 2.25 |
| Potassium nitrate | 0.5 |
| L-arginine | 1.5 |
| Flavor | 0.95 |
| Benzyl alcohol | 0.3 |

The composition may be manufactured as follows: a first tank ("gel tank") is charged with the 70% aqueous sorbitol solution, followed by the addition of the sodium bicarbonate and arginine. Preferably, the mixture is thoroughly agitated until the arginine is completely dispersed, resulting in a homogenous solution. After mixing for about 5 minutes, the water is added, followed by the potassium nitrate. In a separate tank, the sodium monofluorophosphate and sodium saccharin are combined, and this premix is added slowly to the gel tank. After mixing, the carrageenan is slowly added over about 5 minutes with the temperature of the tank maintained at about 60-70° C. and the mixture is agitated for at least 20 minutes. Finally, the sodium silicate is added, and after brief stirring, the entire gel mixture is transferred under a controlled vacuum to the main mixing tank. Thickening silica, PCC, NCC, colors and flavors are then added sequentially with mixing and de-aerating. Finally, SLS is added under vacuum with mixing, followed by additional flavor and the benzyl alcohol under vacuum.

Additional compositions which can be prepared according to the present invention include the following:

TABLE 2

| Ingredient | Weight % |
| --- | --- |
| Sorbitol (70% Aq.) | 10-50% (e.g., 30%) |
| Carrageenan | 0.8 |
| Sweeteners | 0.1-3% |
| Fluoride sources | 0.1-5% |
| pH adjusting agents | 0.1-5% |
| Water | 5-20% |
| Abrasives | 10-60% |
| Thickening agents | 0.1-10% |
| Colorants | 0.1-5% |
| Surfactants | 0.1-5% |
| Desensitizing agents | 0.1-5% |
| L-arginine | 0.1-5% (e.g., 1.5%) |
| Flavorants | 0.1-5% |
| Preservatives | 0.01-5% |

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

The invention claimed is:

1. A method of manufacturing an arginine-based dentifrice comprising the steps of (1) forming a homogenous solution consisting of arginine free base in concentrated aqueous sorbitol and optionally a base, and subsequently (2) combining the arginine/sorbitol solution with one or more other orally acceptable ingredients.

2. The method according to claim 1, wherein the concentrated aqueous sorbitol is a 60-80 wt. % aqueous sorbitol solution.

3. The method according to claim 1, wherein the concentrated aqueous sorbitol consists essentially of sorbitol and water.

4. The method according to claim 1, wherein the arginine is L-arginine.

5. The method according to claim 1, wherein the solution of arginine in concentrated aqueous sorbitol of step (1) consists of arginine, sorbitol, sodium bicarbonate, and water.

6. The method according to claim 1, wherein the solution of arginine in concentrated aqueous sorbitol of step (1) comprises from 1 to 30% w/w of arginine.

7. The method according to claim 1, wherein the solution of arginine in concentrated aqueous sorbitol of step (1) is formed at room temperature.

8. The method according to claim 1, wherein the solution of arginine in concentrated aqueous sorbitol of step (1) is chemically and physically stable for at least 5 days, or at least 2 weeks, or at least 1 month, or at least 3 months.

9. The method according to claim 1, wherein the solution of arginine in concentrated aqueous sorbitol of step (1) is microbially stable for at least 5 days, or at least 2 weeks, or at least 1 month, or at least 3 months.

10. The method according to claim 1, wherein the solution of arginine in concentrated aqueous sorbitol of step (1) has a pH of 7.5 to 11.

11. The method according to claim 1, wherein any one or more of the one or more orally acceptable ingredients are selected from water, abrasives, humectants, surfactants, thickeners, fluoride sources, anticaries agents, desensitizing agents, antibacterial agents, pH adjusting agents, preservatives, colorants, flavorants, and sweeteners.

12. The method according to claim 11, wherein the abrasives are selected from silica, sodium silicate, natural calcium carbonate (NCC), precipitated calcium carbonate (PCC), dicalcium phosphate (DiCal).

13. The method according to claim 11, wherein the fluoride source is selected from sodium fluoride, stannous fluoride and sodium monofluorophosphate.

14. The method according to claim 1, wherein a product of method has a water content of less than 20 wt. % by weight of the composition.

15. The method according to claim 1, wherein a product of the method comprises arginine in an amount of 0.5 to 5 wt. % by weight of the composition.

16. The method according to claim 1, wherein a product of the method comprises sorbitol in an amount of 5 to 90 wt. % by weight of the composition.

17. The method according to claim 1, wherein the solution of arginine in concentrated aqueous sorbitol of step (1) consists of about 1 to about 10 wt. % L-arginine, water, and about 60 to 80 wt. % of sorbitol, by weight of the solution.

18. The method according to claim 17, wherein the solution of arginine in concentrated aqueous sorbitol of step (1) has a pH of about 10.6.

19. The method according to claim 1, wherein the arginine in the homogenous solution is stable at a temperature of 20 to 25° C.

\* \* \* \* \*